(12) United States Patent
Erbacher et al.

(10) Patent No.: US 9,017,557 B2
(45) Date of Patent: Apr. 28, 2015

(54) MONOLITHIC-SHAPED BODIES FOR PURIFYING AND SEPARATING BIOPOLYMERS

(75) Inventors: Christoph Erbacher, Haan (DE);
Christoph Ritt, Langenfeld (DE);
Markus Kirchmann, Essen (DE)

(73) Assignee: Qiagen GmbH, Hilden (DE)

( * ) Notice: Subject to any disclaimer, the term of this patent is extended or adjusted under 35 U.S.C. 154(b) by 2064 days.

(21) Appl. No.: 11/658,481

(22) PCT Filed: Jul. 27, 2005

(86) PCT No.: PCT/EP2005/008132
§ 371 (c)(1),
(2), (4) Date: Oct. 20, 2008

(87) PCT Pub. No.: WO2006/013043
PCT Pub. Date: Feb. 9, 2006

(65) Prior Publication Data
US 2009/0062522 A1 Mar. 5, 2009

(30) Foreign Application Priority Data
Jul. 29, 2004 (EP) .................................... 04018053

(51) Int. Cl.
*C07H 21/02* (2006.01)
*G01N 33/483* (2006.01)
*B01J 20/28* (2006.01)
*B01J 20/283* (2006.01)
*G01N 30/52* (2006.01)

(52) U.S. Cl.
CPC .......... *B01J 20/28042* (2013.01); *B01J 20/283* (2013.01); *B01J 2220/82* (2013.01); *G01N 2030/528* (2013.01)

(58) Field of Classification Search
CPC ............... B01J 20/28042; B01J 20/283; B01J 2220/82; G01N 2030/528
See application file for complete search history.

(56) References Cited

U.S. PATENT DOCUMENTS

| | | | | |
|---|---|---|---|---|
| 5,076,980 A | * | 12/1991 | Nogues et al. | 264/621 |
| 5,624,875 A | * | 4/1997 | Nakanishi et al. | 501/39 |
| 5,863,848 A | * | 1/1999 | Bujalski et al. | 501/88 |
| 6,207,098 B1 | | 3/2001 | Nakanishi et al. | |
| 6,210,570 B1 | | 4/2001 | Holloway | |
| 6,514,454 B1 | * | 2/2003 | Ganguli et al. | 264/621 |
| 6,531,060 B1 | | 3/2003 | Nakanishi et al. | |
| 7,001,568 B2 | * | 2/2006 | Wang et al. | 264/621 |
| 2002/0045693 A1 | * | 4/2002 | Hayashi et al. | 524/394 |

FOREIGN PATENT DOCUMENTS

| | | |
|---|---|---|
| DE | 100 28 572 | 12/2001 |
| GB | 1 501 445 | 2/1978 |

OTHER PUBLICATIONS

Siouffi, A. -M : "Silica Gel-Based Monoliths Prepared by the Sol-Gel Method: Facts and Figures," Journal of Chromatography A, Elsevier Science, vol. 1000 (1-2), pp. 801-818, 2003.

* cited by examiner

*Primary Examiner* — Dirk Bass
(74) *Attorney, Agent, or Firm* — Fanelli Haag & Kilger PLLC

(57) ABSTRACT

The present invention concerns new monolithic shaped bodies, a method for their preparation as well as their use especially for the selective purification and separation of biopolymers. A chromatographic separation material is provided with the new monolithic shaped bodies that allows a selective, efficient and reproducible purification and separation of biopolymers.

18 Claims, 1 Drawing Sheet

MONOLITHIC-SHAPED BODIES FOR PURIFYING AND SEPARATING BIOPOLYMERS

CROSS-REFERENCE TO RELATED APPLICATIONS

This application is a United States national stage filing under 35 U.S.C. §371 of international (PCT) application No. PCT/EP2005/008132, filed Jul. 27, 2005 and designating the U.S., which claims priority to European application 04018053.1, filed Jul. 29, 2004.

FIELD OF THE INVENTION

The present invention concerns new monolithic shaped bodies, a method for their preparation and their use for the purification and separation of biopolymers.

BACKGROUND OF THE INVENTION

Owing to advancing automation and miniaturisation in the area of biotechnology, solutions have been increasingly sought in recent years for the rapid and efficient processing of, especially, minimal amounts of sample. In particular, the use of fully automated, high throughput workstations increasingly demands developments with which very high numbers of samples can be processed in the shortest possible time, while at the same time the smallest amounts of biological material can be detected reproducibly. In this context, the miniaturisation of inter alia filter and separation devices, for example the so-called micro-titre or multi-well plates, are in demand. In addition to the usual 96 well plates, plates with 384 wells and 50 µl volume per well are meanwhile already standard. Moreover, 1536 well plates with volumes of 5 to 10 µl per well have been available for some time.

However, in respect of conventional filter materials for the purification and separation of biopolymers, technical advance has reached its limits with the use of such small wells, especially when the filter and separation materials must exhibit withal very good selective properties and high binding capacities in the purification of biopolymers.

Thus the currently available glass fibre and silica membranes for 96 well plates are of only limited suitability for use in 384 well plates since the filter and separation surfaces would be too small to achieve satisfactory levels of efficiency and binding capacities. Moreover, in addition to increased production expenditure, the punched-out miniature membranes are often too thin and hence too unstable for use in the wells without aids, for example an additional base plate and/or other stabilisation agents that can be inserted into the wells, through which higher production costs are incurred.

In addition, owing to aging, conventional glass fibre and silica membranes loose considerable efficiency, even after a short period of time, so that they are unsuitable for storage over an extended period. Besides, activation of the aged membranes is not only very inconvenient, but frequently not adequate enough to achieve reproducible results.

In this context, in the area of chromatography, monolithic filter and separation materials are currently continually gaining in importance in the preparation of capillary columns. Here, using the so-called sol-gel method, a polymerisable, low-molecular weight compound (sol) is first prepared, which is then converted into aggregated or polymerised material (gel) in polymerisation reactions. The reaction takes place directly in the respective chromatography columns. These methods are, however, solely suitable for capillary columns with a very small diameter (<300 µm), since inorganic monolithic filter and separation material in particular is usually subject to considerable shrinkage, through which a dead volume is created between the monolithic filter and separation material and the separation device, which usually greatly impairs the separation properties of the columns (see DE OS 100 28 572). To remove such dead volumes it has been suggested that after the polymerisation and subsequent aging and drying of the frits, the separation devices are again filled with polymerisation solution and all stages of the preparation method are repeated. However, before a renewed polymerisation can be carried out the aged frit material must first be reactivated with an activation solution, which overall leads to a very time and cost intensive preparation process.

A further disadvantage of these multiply polymerised monolithic frits is also that owing to their construction they are less stable and consequently the abrasion of the monolithic material also increases with increasing diameter of the filter or separation device. In particular, the use in association with pressure devices frequently leads to contamination through increased abrasion, which in turn can lead to interference in the following analysis steps, or even to corrupted results.

In order to overcome the above described disadvantages in the state of the art of known chromatographic separating material, the object forming the basis of the present invention is to provide a stable filter and separation material that allows selective purification and separation of biopolymers as well as an efficient and reproducible processing of a large number of samples, especially in automated and/or miniaturised analytical procedures. The filter and separation material should also be stable in storage and be rapidly utilisable after long storage.

SUMMARY OF THE INVENTION

This object was solved by the provision according to the invention of monolithic shaped bodies obtained by a method comprising the following process steps:
  a) placing silicon dioxide into a reaction vessel;
  b) addition of a solution A comprising at least one or more alkali silicate(s) and potassium borate,
  c) addition of a solution B comprising at least one or more porogen(s) and water,
  d) addition of at least one organic amide and
  e) drying of the reaction mixture.

DETAILED DESCRIPTION OF THE INVENTION

Figure 1:
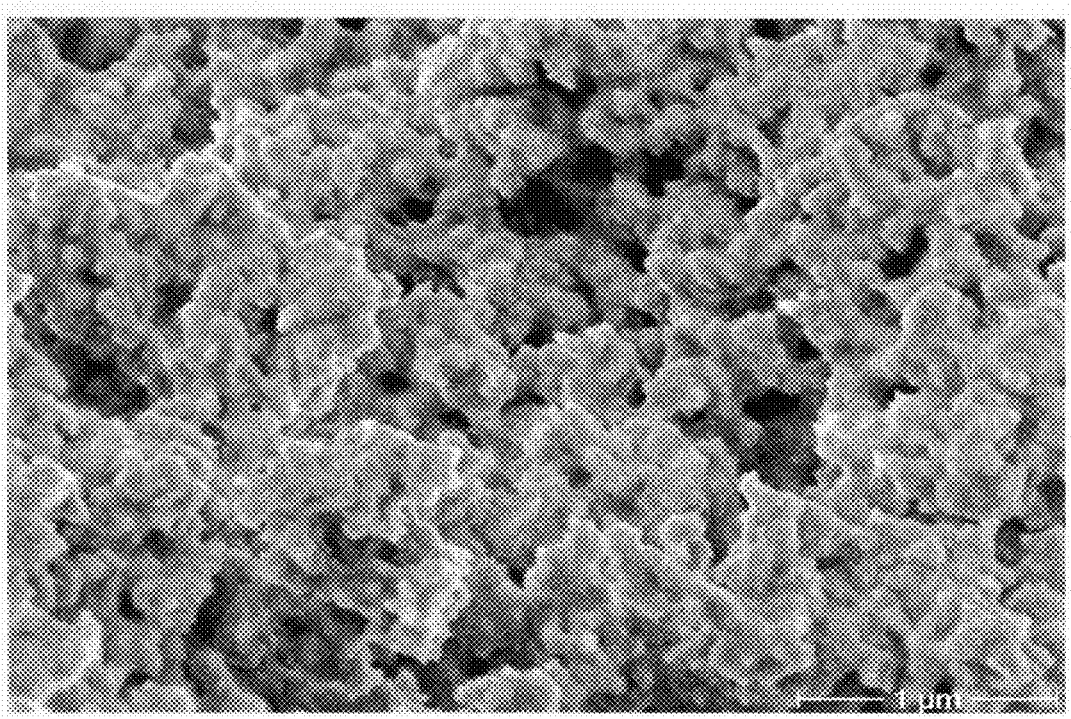
FIG. 1 the structure of the monolithic shaped body according to the invention with PEG as porogen under the electron microscope.

The above named monolithic shaped bodies are obtained according to the invention by a polymerisation process. According to process step a) a colloidal silica gel is first placed into a reaction vessel. According to a preferred embodiment of the invention the silicon dioxide is the added in the form of aqueous silicon dioxide dispersions or silica gels. Various commercially available silicon dioxide dispersions can be used which differ from one another in particle size, silicon dioxide content and the type of stabilisation (e.g.

stabilisation in ammonia, sodium hydroxide solution, etc.). In addition to agglomerated silica gels, colloidal silica gels can be used according to the invention. Within the meaning of the invention agglomerated means that cross-linked, non-porous, spherical silicon dioxide with a mean particle diameter of about 40 nm is present in water. According to a particularly preferred embodiment of the invention the silicon dioxide is present in the form of aqueous colloidal dispersions of small silicon dioxide particles. These are mono- or polydispersed colloidal silicon dioxide dispersions such as, for example, Ludox (W.R. Grace & Co., Columbia, US), or Levasil (Bayer AG, Leverkusen, DE) etc., wherein within the meaning of the invention colloidal means that non-cross-linked, individual spherical silicon dioxide particles are present in water. Preferably, such a colloidal dispersion comprises 30-50 percent by weight, preferably 40-45 percent by weight silicon dioxide particles with a mean particle diameter of 5-100 nm, preferably 10-40 nm, particularly preferably 15-25 nm.

According to process step b) of the method of the invention a solution A is next added to the silicon dioxide present. This comprises at least one or more alkali silicate(s) and commercial potassium borate (Honeywell Special Chemicals (GmbH, Seelze, DE). As was surprisingly discovered, the addition of potassium borate in particular to the monolithic shaped bodies according to the invention leads to improved binding properties at the pore surfaces of the mesopores and thus conjointly to a higher yield of isolated biopolymers. However, in order to dissolve the potassium borate in the reaction mixture it is preferably dissolved in an alkali silicate solution. Within the meaning of the invention alkali silicates are understood to be alkali salts of silicic acid, especially sodium and potassium silicate. According to a preferred embodiment of the invention, in the preparation of solution A 0.1 to 4 percent by weight, preferably 0.5 to 2 percent by weight, especially preferably 0.5 to 1.0 percent by weight potassium borate (relative to the total reaction mixture) is dissolved, preferably in a commercial colourless colloidal potassium silicate solution such as, for example, potassium silicate 28°/30°Bé (28/30 Baumé grade, which corresponds to a density of 1.240/1.261 g/cm$^3$) from Cognis Deutschland GmbH & Co. KG., Düsseldorf, DE with a preferred silicon dioxide content of 20.5%.

To achieve further a greater mechanical stability of the monolithic shaped bodies according to the invention permanent macroporous polymers are required. These are formed by the presence of suitable porogens in the dispersed phase. Therefore, a further process step c) a solution B comprising at least one or more porogen(s) and water are added. Water soluble chemical compounds are beneficially used as added pore building substances (so-called pore builders or porogens). Highly water soluble or miscible tensides and/or emulsifiers are particularly suitable. Such pore builders are known. The porogens used in accordance with the invention should be thermodynamically good solvents for the monomer, but poor solvents for the polymer, since these lead to a very late phase separation. In this way the homogeneity of the reaction mixture is beneficially ensured, which leads to the preparation of monolithic shaped bodies with very stable permeable membranes. Whereas primarily membranes of interconnected, continuous macropores are produced by the addition of the porogens, the mesopores located in the walls of the macropores are formed by the added colloid.

According to a preferred embodiment of the invention polyalcohols are preferably used as porogens in the preparation of solution B. Ethylene glycol, diethylene glycol, glycerol and/or diglycerol are particularly suitable; but also polypropylene glycol (PPG) and/or polyethylene glycol (PEG). All above named compounds can be present individually or as mixtures.

Surprisingly, the stability of the monolithic shaped bodies formed according to the invention can be greatly increased by the addition of one or more of the above-named porogen(s) dissolved in water. Here the volume of the water (distilled or fully de-ionised) has a considerable influence upon pore formation. Depending on the porogen used, about 1 to 4 ml water, preferably 2 to 3 ml water, are used beneficially to dissolve the porogen or for the preparation of 5-40%, preferably 10-20%, porogen solutions.

In this connection the use of a mixture of PEG (e.g. PEG 3000/Fluka, Buchs, CH) and glycerol (Merck KGaA, Darmstadt, DE) or diglycerol (Fluka, Buchs, CH) with water has proved to be most particularly beneficial. The monolithic shaped bodies thus prepared exhibit pores with an optimal mean pore diameter and a narrow pore size distribution. This leads beneficially to an increase in the specific surface and thus conjointly to an increase in the binding capacities of the monoliths according to the invention. Moreover, an abrasion of the monolithic shaped body formed can be reduced considerably or even avoided by the addition of glycerol and/or diglycerol, for example during a filtration procedure, etc., above all during the additional use of pressure apparatus. Moreover, the increase in the amount of glycerol leads to a more uniform structure of the monoliths according to the invention.

As is known from current sol-gel processes, a substance that lowers the pH value, for example an organic or inorganic acid, is added as initiator to the reaction mixture (sol) to start gel formation, that is, for the transformation of the sol form of the reaction mixture into the gel form. However, organic or inorganic acids have the disadvantage that they cause a very rapid fall in the pH value, which consequently leads to immediate gel formation which, depending on the shape and size of the monolithic shaped body to be formed, can be uneven or even incomplete. In particular, the transfer of the reaction mixture into corresponding moulding devices requires a time-delayed gel formation. Within the meaning of the invention moulding devices are understood to be on the one hand commercial devices used for the purification and separation of biopolymers, for example spin columns, multi-well plates, pipette tips, etc., and on the other moulding devices for the production of frits, pellets or all other conceivable shapes of the monolithic filter and separation materials (for example, spheres, cylinders, etc.). According to a preferred embodiment of the invention a low molecular weight compound that decomposes thermally under basic conditions and which lowers the pH value of the reaction mixture through its hydrolysis is added to the reaction mixture to initiate the polycondensation reaction. It was surprisingly found that the use of organic amides in particular allows beneficial uniform and slow gel formation. Thus, in a particularly preferred embodiment of the invention, at least one organic amide (for example polyacrylamide, acetamide, urea, formamide, etc.) is subsequently slowly added to the reaction mixture in accordance with process step d). In this context the use of commercial formamide and/or urea (Merck KGaA, Darmstadt, DE) is most especially beneficial, since these compounds decompose with the formation of low molecular weight compounds that escape during the preparation procedure, or afterwards can be removed readily from the monolithic shaped body formed and thus do not lead to interference during analyses carried out with the monoliths according to the invention or to corrupted results.

An even greater advantage of these compounds is that a reaction mixture treated with formamide and/or urea can be transferred to the respective moulding device within 30 minutes after their addition without deleterious effect on the gel formation process.

After successful transfer or polymerisation of the reaction mixture in the moulding device appropriate to the later intended use the gel shapes are dried in accordance with process step e) for formation of the monolithic shaped bodies according to the invention. Drying is carried out for about 12 to 25 h, preferably 17 to 22 h, especially preferably up to 20 h at 30 to 80° C., preferably at 40 to 60° C. in an appropriate drying device, for example an oven, a drying cabinet or a drying chamber, etc.

During process steps a) to d) the reaction mixture is beneficially kept in constant motion, for example by shaking, stirring, vortexing or by the use of ultrasound, etc., in order to achieve a homogeneous distribution of the educts in the reaction mixture and thus conjointly ensure a uniform structure formation of the monolithic shaped bodies according to the invention.

On the basis of the preparation procedure according to the invention it is thus possible to prepare monolithic filter and separation materials with pre-adjusted pore size and pre-adjusted pore size distribution. These show clear advantages during use as chromatographic separation materials for the purification and separation of biopolymers. In particular, in contrast to conventional filter and separation materials such as glass fibre membranes, the monoliths according to the invention are characterised by greater stability and binding capacity.

Surprisingly these beneficial properties of the monolithic shaped bodies formed according to the invention are augmented by the incorporation of boron—in the form of potassium borate—into the filter material. In particular, the formation of an beneficial pore size of the mesopores during the preparation of the monolithic shaped bodies according to the invention can be influenced or even controlled by the addition of boron compounds.

Particularly beneficial filter and separation properties, such as significant increase in the binding capacity, were shown by monolithic shaped bodies according to the invention that have a weight fraction of 0.1 to 0.3% boron, preferably of 0.15 to 0.25% boron, especially preferred of 0.18 to 0.22% boron.

A further advantage of the method described above is that the educts needed for the formation of the monolithic shaped bodies according to the invention can be introduced simply and quickly into very small shape-giving devices, for example pipette tips or 384 multi-well plates, etc., and the monolithic shaped bodies can be formed in situ.

Furthermore, the use of the most different moulding devices is also effective and inexpensive. Unlike conventional glass fibre plates (especially in the 384 multi-well format) the shaped bodies prepared according to the invention can be prepared with any structure without clamp rings and base plates more economically and more rapidly. In addition the shaped bodies prepared according to the invention can be easily replaced by new after use, which leads further to cost savings on materials. Furthermore, pellet production in particular is to be preferred for a rapid and flexible use of the monolithic shaped bodies according to the invention. They have the same good and reproducible separation properties and can also be readily varied in diameter and density.

Furthermore, within the context of the present invention it was found surprisingly that the monolithic shaped bodies according to the invention are equally suited as chromatographic separation material for the selective separation of biopolymers. This is achieved in the first instance by the targeted adjustment of the pore size of the mesopores. In a further embodiment according to the invention, however, the bonding chemistry within the mesopores is optionally influenced in such as way that one or more transition metal(s) can be incorporated into the structure of the monolithic shaped bodies according to the invention or attached to the surface of the pores formed in the monolithic shaped bodies according to the invention. For this purpose an aqueous solution C comprising one or more transition metal salts is prepared in advance of the method according to the invention.

For incorporation of the transition metals into the monolithic shaped bodies of the invention the solution C is mixed with solution A at the beginning of the method according to the invention. As became apparent, aqueous solutions of copper, zinc, and/or manganese salts are particularly suitable, preferably solutions with 0.2 to 1.7 percent by weight copper sulphate or 0.8 to 2.9 percent by weight potassium permanganate.

For attachment the transition metals especially to the surface of the mesopores formed in the monolithic shaped bodies according to the invention the dried filter or separation material is soaked with the solution C and dried for ca. 18 hr at room temperature. Alternatively, depending on the materials properties, a more rapid drying can be carried out at 130° C. (s. Example 1b and 3). The solutions used are essentially solutions of zirconium and/or titanium salts, preferably 1-10% $ZrCl_4$ or $TiCl_4$ solutions, wherein these compounds can also be dissolved in other normal solvents (e.g. diethyl ether, THF, etc.).

In summary, it emerges that according to a preferred embodiment of the present invention, the monolithic shaped bodies according to the invention are prepared with a reaction mixture of the following composition (details in percent by weight):

35 to 85% potassium silicate,
0.1 to 25% of at least one colloidal silica gel,
0.1 to 30% water,
0.1 to 12% at least one porogen,
6 to 12% at least one organic amide,
0.1 to 5% potassium borate,
0 to 10% of a salt of at least one transition metal.

The reaction mixture with the following composition is particularly preferred (details in percent by weight):

50 to 60% potassium silicate (28/30),
5 to 10% of at least one colloidal silica gel,
10 to 25% water,
3 to 6% polyethylene glycol and/or diethylene glycol,
5 to 10% formamide and/or urea,
0.5 to 2% potassium borate,
0 to 2% glycerol, and
0 to 10% of a salt of at least one transition metal.

In the following the present invention will be illustrated more closely by means of the appended diagrams and further experimental details in the embodiment examples.

Figure 2:
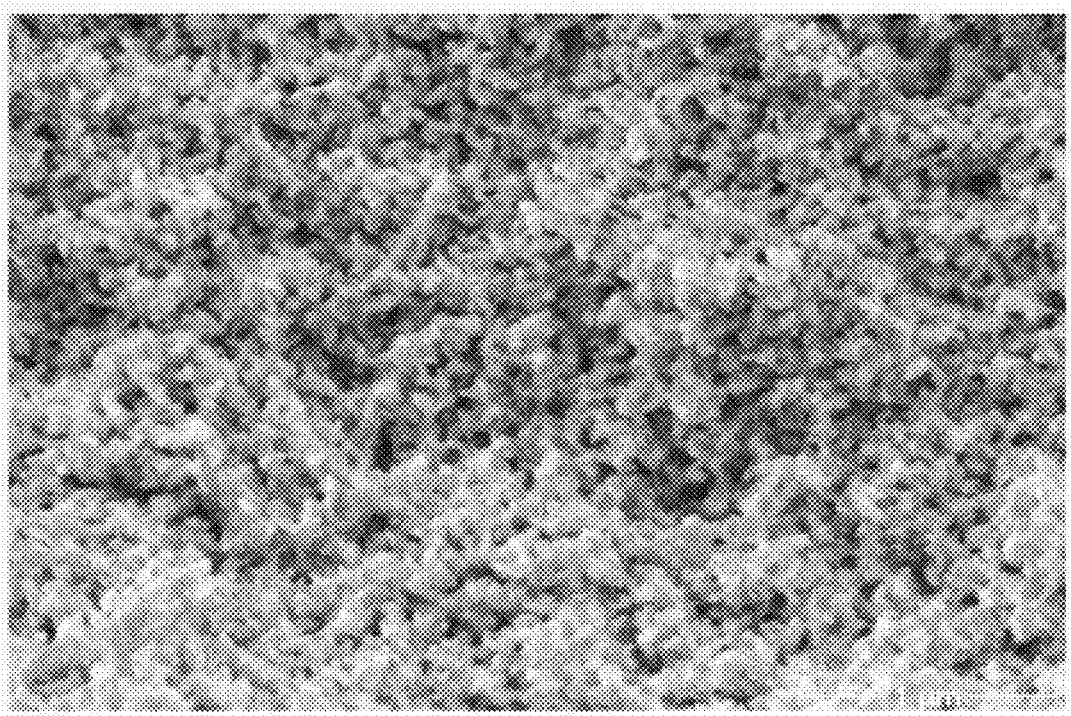
FIG. 2 the structure of the monolithic shaped body according to the invention without porogen under the electron microscope.

Illustrated is:

FIG. 1 the structure of the monolithic shaped body according to the invention with PEG as porogen under the electron microscope;

FIG. 2 the structure of the monolithic shaped body according to the invention without porogen under the electron microscope;

It can be clearly seen from the photographs of the monolithic shaped bodies according to the invention shown in FIG. 1 and FIG. 2 that significantly larger macropores develop by the addition of polyethylene glycol to the reaction mixture, which indicates a better flow rate. The determination of the pore size of the macro- and mesopores and their respective specific surfaces is carried out by electron microscopy. The specific surface of the samples is about 10 $m^2g^{-1}$.

EMBODIMENT EXAMPLES

Example 1

General Preparation of the Monoliths According to the Invention

Firstly a solution A and a solution B were prepared (s. Table 1). Different amounts of a commercial colloidal silicon dioxide were then placed in a 50 ml PE vessel into which solution A and solution B were slowly pipetted with constant shaking for sol formation. Different amounts of formamide (see Table 1) were added to the slightly cloudy but precipitate-free reaction mixture (RG) for gel formation. Next, within 30 minutes of the addition of the organic amide, 150 µl each time of the reaction mixture were pipetted into either (1) a commercial spin column or (2) into the holes of a commercial well plate, the outlets of which were initially closed (for example with adhesive tape, etc.) After polymerisation the upper inlets of some of the moulding devices were also covered. Finally, the moulding devices were warmed in a drying cabinet for 20 h at 40° C.

It was demonstrated that by covering the moulding devices during the polycondensation and/or the drying procedure a slower drying out of the monolithic shaped bodies according to the invention took place, which enhanced further a more consistent formation of the monolithic structure.

a) Use of Different Moulding Devices (1) The monoliths obtained in the spin columns completely filled the lower region of the spin columns. By inserting clamp rings the monoliths were fixed in the spin column and were used directly for the isolation of genomic DNA and RNA from blood samples, rat liver tissue and rat brain tissue.

(2) The monolith pellets obtained from the well plate were removed from the well plates and fixed into the spin columns. The spin columns thus prepared were used directly for the isolation or genomic DNA and RNA from blood samples, rat kidney tissue and rat brain tissue. In order to ensure particularly good fixture of the pellets in the spin columns, well plates were used for the preparation of the pellets the diameters of which were larger than the internal diameter of the spin columns. This made the use of clamp rings superfluous and the method thus more cost effective.

b) Drying Times of the Monoliths According to the Invention

To investigate the drying times of the monoliths according to the invention the gel prepared was placed in the moulding devices and these were warmed in the drying cabinet at ca. 40° C. A check was carried out hourly to determine how long the monolithic frits (shaped bodies) being formed needed for drying. On the basis of the experimental series carried out, it was possible to demonstrate that the monoliths according to the invention hardened after a reaction time of ca. 2 h and had a certain stability. However, they were still insufficiently stable to prevent silica abrasion in a way that successful analysis results could have been obtained with them. The full capacity of the frits was first achieved after 17 to 20 h.

It was demonstrated further that drying times can play a role in shrinkage. High temperatures and rapid drying times resulted in the shrinkage being less than with slow drying at low temperature. The limit of the drying temperature is often determined by the material of the moulding material. That means, if the as yet undried shaped bodies are taken from the moulding device, temperatures of up to 400° C. are appropriate.

It was also investigated if whether and to what extent a possible phase separation of the reaction mixture can be prevented during drying with, for example, microwave irradiation or the use of thermomixers, for it had been shown that separation of the reaction mixtures could be inhibited by permanent shaking during gelling. This led beneficially to a significantly more homogeneous structure of the monoliths according to the invention and thus to a higher capacity. It was found to be particularly beneficial to polycondense the samples completely in a thermomixer at 30 to 70° C., preferably 40 to 60° C.

In order to ensure that no preparation-related impurities from the monolithic shaped bodies according to the invention interfered with the analysis results during a separation step, particularly during sensitive analysis procedures, the monolithic shaped bodies formed were subsequently optionally rinsed again once or several times with distilled water and then dried at 40 to 120° C.

c) Comparison of Monoliths Prepared According to the Invention

In order to be able to compare the monoliths prepared according to the invention with one another, monoliths were prepared from a series of reaction mixtures of different composition and their properties were investigated. This following selection is exemplary and serves to illustrate the special properties of the monoliths according to the invention.

TABLE 1

Compositions of reaction mixtures for the preparation of monoliths according to the invention

| Reaction mixture (RG) | Solution A | Solution B | Silicon dioxide (Ludox AS 40, particle size 20 nm, 40 wt % $SiO_2$) | Formamide |
|---|---|---|---|---|
| RG 1 | 32.7 mg potassium borate dissolved in 4 ml potassium silicate | 400 mg PEG 3000 dissolved in in 2 ml water | 0.5 ml | 0.5 ml |
| RG 2 | 65.45 mg potassium borate dissolved in 4 ml potassium silicate | 400 mg PEG 3000 dissolved in in 2 ml water | 0.5 ml | 0.5 ml |
| RG 3 | 32.7 mg potassium borate dissolved in 3.5 ml potassium silicate | 400 mg PEG 3000 dissolved in in 2 ml water | 1 ml | 0.5 ml |
| RG 4 | 65.45 mg potassium borate dissolved in 3.5 ml potassium silicate | 400 mg PEG 3000 dissolved in in 2 ml water | 1 ml | 0.5 ml |

TABLE 1-continued

Compositions of reaction mixtures for the preparation of monoliths according to the invention

| Reaction mixture (RG) | Solution A | Solution B | Silicon dioxide (Ludox AS 40, particle size 20 nm, 40 wt % $SiO_2$ | Formamide |
|---|---|---|---|---|
| RG 5 | 4 ml potassium silicate | 400 mg PEG 3000 dissolved in in 2 ml water | 0.5 ml | 0.5 ml |
| RG 6 | 65.45 mg potassium borate dissolved in 4 ml potassium silicate | 400 mg PEG 3000 dissolved in in 2 ml water | 0.5 ml | 0.6 ml |
| RG 7 | 65.45 mg potassium borate dissolved in 4 ml potassium silicate | 400 mg PEG 3000 dissolved in in 2 ml water | 0.5 ml | 0.7 ml |
| RG 8 | 65.45 mg potassium borate dissolved in 4 ml potassium silicate | 360 mg PEG 3000 and 40 mg glycerol dissolved in 2 ml water | 0.5 ml | 0.5 ml |
| RG 9 | 65.45 mg potassium borate dissolved in 4 ml potassium silicate | 320 mg PEG 3000 and 80 mg glycerol dissolved in 2 ml water | 0.5 ml | 0.5 ml |
| RG 10 | 65.45 mg potassium borate dissolved in 4 ml potassium silicate | 280 mg PEG 3000 and 120 mg glycerol dissolved in 2 ml water | 0.5 ml | 0.5 ml |
| RG 11 | 65.45 mg potassium borate dissolved in 4 ml potassium silicate | 360 mg PEG 3000 and 40 mg diglycerol dissolved in 2 ml water | 0.5 ml | 0.5 ml |
| RG 12 | 65.45 mg potassium borate dissolved in 4 ml potassium silicate | 320 mg PEG 3000 and 80 mg diglycerol dissolved in 2 ml water | 0.5 ml | 0.5 ml |
| RG 13 | 65.45 mg potassium borate dissolved in 4 ml potassium silicate | 280 mg PEG 3000 and 120 mg diglycerol dissolved in 2 ml water | 0.5 ml | 0.5 ml |
| RG 14 | 65.45 mg potassium borate dissolved in 4 ml potassium silicate | 200 mg PEG 3000 dissolved in in 1 ml water | 0.5 ml | 0.5 ml |

In addition to tests for stability and abrasion as well as optical tests for colour and shape, primarily capacity tests were carried out. For this purpose genomic deoxyribonucleic acid (gDNA) and/or ribonucleic acid (RNA) in particular were purified from different biological samples. Purification was carried out with the monolithic column materials prepared according to the invention and with conventional glass fibre column material as reference. Preferably Rneasy and Qiaprep (QIAGEN GmbH, Hilden, DE) were used as reference material. In addition, depending on sample material purification was carried out in accordance with the respective current purification protocols, for example the "QIAamp DNA Blood Mini protocol" or the "RNeasy MINI protocol" etc.

On the basis of capacity measurements with monoliths prepared from reaction mixtures RG 1 to 5 predictions could be made, for example, on the influence of individual substances. Thus, according to Table 2 the use of potassium borate, for example, contributed considerably to the increase in capacity of the monoliths according to the invention.

TABLE 2

Influence of potassium borate

| Column material from RG | Capacity in µg |
|---|---|
| RG 1/1 | 7.14 |
| RG 1/2 | 7.95 |
| RG 2/1 | 8.15 |
| RG 2/2 | 8.63 |
| RG 3/1 | 6.64 |
| RG 3/2 | 5.56 |
| RG 4/1 | 5.68 |
| RG 4/2 | 4.96 |

TABLE 2-continued

Influence of potassium borate

| Column material from RG | Capacity in µg |
|---|---|
| RG 5/1 | 0.36 |
| RG 5/2 | 0.73 |
| QIAQuick | 6.45 |

It was established that through the use of potassium borate in the monoliths according to the invention an increase of up to 30% and more was achieved in the capacity compared with the capacities of conventional spin column materials.

Equally, it could also be shown that the properties of the monoliths according to the invention could be further improved by the change in the amount of formamide in the reaction mixture. Thus abrasion could be totally avoided without losses in capacity through the increase in the amount of formamide.

TABLE 3

Change in formamide amounts

| Column material from RG | Capacity in µg |
|---|---|
| RG 2/1 | 20.7 |
| RG 2/2 | 29.6 |
| RG 6/1 | 27.4 |
| RG 6/2 | 26.7 |
| RG 7/1 | 26.8 |
| RG 7/2 | 27.6 |
| QIAQuick | 16.1 |

Also the variation in different amounts of porogens contributed to the improvement in monolith structure. It emerged that through the addition of, in particular, glycerol and/or diglycerol the monolith structure became more homogeneous. Moreover, the addition of glycerol and/or diglycerol also contributed to the prevention of abrasion.

TABLE 4

Effect of glycerol

| Column material from RG | Capacity in µg |
|---|---|
| RG 2/1 | 22.9 |
| RG 2/2 | 21.3 |
| RG 8/1 | 22.6 |
| RG 8/2 | 22.6 |
| RG 9/1 | 24.3 |
| RG 9/2 | 22.8 |
| RG 10/1 | 20.2 |
| RG 10/2 | 23.8 |
| QIAQuick | 13.1 |

TABLE 5

Effect of diglycerol

| Column material from RG | Capacity in µg |
|---|---|
| RG 2/1 | 27.3 |
| RG 2/2 | 25.4 |
| RG 11/1 | 22.3 |
| RG 11/2 | 11.0 |
| RG 12/1 | 11.3 |
| RG 12/2 | 21.1 |
| RG 13/1 | 21.6 |
| RG 13/2 | 20.8 |
| QIAQuick | 15.6 |

As a further advantage of a more homogeneous monolith structure it emerged that the use of porogens also brought about a significant increase in RNA yield (see also Example 2).

Example 2

Preparation of RNA Selective Monoliths a) Preparation of RNA Selective Monoliths Comprising Copper Sulphate For the preparation of a solution C 15.9 mg copper sulphate (Fluka, Buchs, CH) and 39.8 mg potassium tartrate (Fluka, Buchs, CH) were dissolved in 0.5 ml water and treated slowly with 15.0 mg potassium hydroxide (Fluka, Buchs, CH). The resulting blue suspension was pipetted into a solution A prepared as in Example 1 with vortexing. A clear blue solution was produced. This was pipetted slowly into 0.5 ml colloidal silicon dioxide contained in a 50 ml polyethylene vessel. Next, also with vortexing, a solution B comprising 360 mg PEG 3000 and 40 mg glycerol dissolved in 2 ml water was added slowly. After the addition of 0.5 ml formamide, 100 µl each time of the solution was pipetted into the correspondingly prepared spin columns and warmed in a drying cabinet for 20 h at 40° C. A gDNA-free and reproducible RNA isolation from tissue samples was achieved.

Sample 1: The RNA content in 20 mg rat kidney tissue was determined according to the Fibrous Tissue protocol (QIAGEN GmbH, Hilden, DE):

Yield: a) 20 µg total RNA per 10 mg tissue. (no gDNA contamination)
b) 19 µg total RNA per 10 mg tissue. (no gDNA contamination)
c) 19 µg total RNA per 10 mg tissue. (no gDNA contamination)
d) 20 µg total RNA per 10 mg tissue. (no gDNA contamination)

b) Preparation of RNA Selective Monoliths Comprising Potassium Permanganate

For the preparation of a solution C 0.0625 g potassium permanganate (Fluka, Buchs, CH) were dissolved in 0.5 ml deionised water. The potassium permanganate solution was pipetted with vortexing into a solution A prepared as in Example 1. 0.5 ml of a colloidal silica gel was then placed into a 50 ml polyethylene vessel and the above mixture of potassium silicate and potassium permanganate was slowly pipetted in. Then, again with vortexing, a solution B comprising 360 mg PEG 3000 and 40 ml glycerol in 2 ml deionised water was added. Finally, 0.5 ml formamide was added slowly and pipetted into respectively prepared spin columns. After a drying time of 20 h at 40° C. in a drying cabinet the resulting monoliths could be used for the isolation of RNA from different tissues. A gDNA-free and reproducible RNA isolation from different tissue samples was achieved.

Sample 2: The RNA content in 40 mg rat brain tissue was determined according to the Lipid Tissue protocol (QIAGEN GmbH, Hilden, DE):

Yield: a) 7 µg total RNA per 10 mg tissue. (no gDNA contamination)
b) 8 µg total RNA per 10 mg tissue. (no gDNA contamination)

c) Preparation of RNA Selective Monoliths by Additional Coating

For the coating of the surface of monolithic shaped bodies according to the invention prepared from RG 2 as in the example the dried filter or separating materials were soaked with two different solutions. In one case the monolithic shaped bodies were placed in a 5% zirconium tetrachloride/THF solution (L1) for 18 h ???, and in the other in a 5% zirconium(IV) isopropoxide–isopropanol complex/ethanol solution (L2).

After a drying time of about 18 h at room temperature the resulting monoliths (M1 and M2) could be used for the isolation of RNA from different tissues. (M1 and M2 were compared with un-coated monolithic shaped bodies from RG 2/M0).

Sample 3: The RNA content of 20 mg rat kidney tissue was determined according to the Rneasy Fibrous Tissue protocol (QIAGEN GmbH, Hilden, DE) (1). In a second experimental procedure (2) a washing step with twice as much GITC (1.8 M) was carried out prior to the washing step RW1, and in a third experimental procedure (3) a washing step with half as much GITC (0.45 M) was carried out after the washing step RW1.

Yield in µg: (per 10 mg tissue)

| | (1) | (2) | (3) | gDNA contamination |
|---|---|---|---|---|
| M0 | 18 | 16 | 14 | detectable |
| M1 | 8 | 15 | 10 | not detectable |
| M2 | 3 | 3 | 13 | very weakly detectable |

A selective, that is gDNA-free, RNA isolation was also achieved from tissue samples with different washing buffers.

Example 3

Different Filling Volumes in the Moulding Devices

For comparison, in addition to 150 µl, 100 µl of the prepared reaction mixture RG2 were placed in spin column and warmed at 40° C. for 20 h in a drying cabinet. Next the capacities of the monolithic shaped bodies according to the invention were compared to those of the QIAQuick spin columns (QIAGEN GmbH, Hilden, DE).

TABLE 6

Different filling volumes

| Column material from RG | Capacity in µg |
|---|---|
| RG 2a1 | 56.2 |
| RG 2a/2 | 52.3 |
| RG 2b/1 | 29.1 |
| RG 2b/2 | 24.5 |
| QIAQuick | 32.1 |

It was demonstrated that in spite of the reduction in the volume used the spin columns with the monolithic shaped bodies had comparable capacities to those of the QIAQuick spin columns. Also, experiments with 50 µl filling volumes and smaller were very successful so that smaller purification devices such as, for example, 384 multi-well plates could be beneficially loaded with the monolithic shaped bodies according to the invention.

Moreover, abrasion of the monolithic material could be prevented completely with smaller filling volumes.

In addition, it could be shown that the monolithic material is significantly more stable than current glass fibre and silica membranes, so that especially in miniaturisation of the filter and separation materials aids such as, for example, additional base plates or clamp rings could be dispensed with. In addition to a reduction in material costs, this also led beneficially to a more rapid preparation of the filter and separation materials.

Sample 4:

100 µl each time of reaction mixture RG 2 were pipetted into spin columns. The spin columns were dried at 40° C. for 20 h in a drying cabinet. Monoliths were obtained that filled the lower region of the spin column. The monoliths were fixed in the spin columns by insertion of clamp rings and used directly for the purification of gDNA from blood. For this 200 µl whole blood were purified according to the QIAamp DNA Blood Mini protocol (QIAGEN GmbH, Hilden, DE). The necessary reagents were also adopted from the QIAamp kit (QIAGEN GmbH, Hilden, DE).

Yield: a) 8.7 µg gDNA
b) 10.4 µg gDNA,
c) 8.5 µg gDNA,
d) 10.5 µg gDNA,

Example 4

Aging of Monolithic Shaped Bodies

In this case monolithic shaped bodies according to the invention (prepared from reaction mixture RG 2) were aged for an extended standing period in the drying cabinet. Of 30 monolithic frits prepared, 15 items were dried for a further 40 hours at 60° C. in the drying cabinet (air circulation stage 3). No difference between the standard frits and the additionally dried frits could be established optically. In addition, even after extended storage at room temperature there were no indications of age-related capacity losses.

The invention claimed is:

1. A filter and separation monolithic shaped body comprising silicon dioxide, macropores and borate having a weight fraction of 0.1 to 0.3% boron obtained by a method comprising the following process steps:
    a) placing silicon dioxide into a reaction vessel;
    b) adding solution A comprising at least one or more alkali silicate(s) and potassium borate,
    c) adding solution B comprising at least one or more porogen(s) and water,
    d) adding at least one organic amide to create a reaction mixture, and
    e) drying the reaction mixture, thereby forming said macropores.

2. The filter and separation monolithic shaped body of claim 1, wherein said monolithic shaped body contains 0.15 to 0.25% boron.

3. The filter and separation monolithic shaped body of claim 1, wherein said monolithic shaped body contains 0.18 to 0.22% boron.

4. The filter and separation monolithic shaped body of claim 1, wherein one or more polyalcohols are used as porogens.

5. The filter and separation monolithic shaped body of claim 1, wherein said organic amide is formamide or urea or a mixture thereof.

6. The filter and separation monolithic shaped body of claim 1, wherein the reaction mixture is dried for up to 20 hours at 40° C. to 60° C.

7. The filter and separation monolithic shaped body of claim 1, wherein said process is further characterised in that an aqueous solution C comprising one or more transition metal salts is added to solution A.

8. The filter and separation monolithic shaped body of claim 7, wherein said solution C is selected from aqueous solutions of copper, zinc, and/or manganese salts, and combinations of such salts.

9. The filter and separation monolithic shaped body of claim 1, wherein the reaction mixture is 35 to 85% potassium silicate, 0.1 to 25% of at least one colloidal silica gel, 0.1 to 30% water, 0.1 to 12% of at least one porogen, 6 to 12% at least one organic amide, 0.1 to 5% potassium borate, 0 to 10% of a salt of at least one transition metal.

10. The filter and separation monolithic shaped body of claim 1, wherein the reaction mixture is 50 to 60% potassium silicate (28/30), 5 to 10% of at least one colloidal silica gel, 10 to 25% water, 3 to 6% polyethylene glycol and/or diethylene glycol, 5 to 10% formamide and/or urea, 0.5 to 2% potassium borate, 0 to 2% glycerol, and 0 to 10% of a salt of at least one transition metal.

11. A process for separation of biopolymers comprising:
    contacting a solution containing the biopolymers with a chromatographic separation material comprising the filter and separation monolithic shaped body of claim 1.

12. A chromatographic separation material for the selective separation of biopolymers comprising the filter and separation monolithic shaped body of claim 1.

13. The filter and separation monolithic shaped body of claim 4, wherein said polyalcohol is selected from the group of ethylene glycol, diethylene glycol, polypropylene glycol, polyethylene glycol, glycerol, diglycerol, and mixtures thereof.

14. The filter and separation monolithic shaped body of claim 1, wherein said filter and separation monolithic shaped body comprises permanent macropores.

15. The filter and separation monolithic shaped body of claim 14, wherein the permanent macropores further comprise mesopores.

16. The filter and separation monolithic shaped body of claim 1, wherein the porogen is a polyethylene glycol (PEG).

17. The filter and separation monolithic shaped body of claim 1, wherein the monolithic shaped body is an RNA selective monolith comprising copper sulphate.

18. The filter and separation monolithic shaped body of claim 14, wherein the macropores have a pre-adjusted pore size and pre-adjusted pore size distribution.

* * * * *